United States Patent
Wang et al.

(10) Patent No.: US 11,326,954 B1
(45) Date of Patent: May 10, 2022

(54) METHOD AND DEVICE FOR MEASURING INTERNAL TEMPERATURE OF HEAP FERMENTATION BASED ON INFRARED TEMPERATURE MEASUREMENT

(71) Applicant: JIANGSU UNIVERSITY, Zhenjiang (CN)

(72) Inventors: Jizhang Wang, Zhenjiang (CN); Han Mao, Zhenjiang (CN); Xu Wang, Zhenjiang (CN); Pingping Li, Zhenjiang (CN); Jing Zhou, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 17/547,268

(22) Filed: Dec. 10, 2021

(30) Foreign Application Priority Data

Dec. 11, 2020 (CN) .......................... 202011450862.6

(51) Int. Cl.
  *G01J 5/00* (2022.01)
  *G01J 5/02* (2022.01)
  *C12M 1/34* (2006.01)
  *G06V 10/26* (2022.01)

(52) U.S. Cl.
  CPC ........... *G01J 5/0003* (2013.01); *C12M 41/12* (2013.01); *G01J 5/0275* (2013.01); *G01J 2005/0077* (2013.01); *G06V 10/267* (2022.01)

(58) Field of Classification Search
  CPC .. G01J 5/003; G01J 5/0275; G01J 2005/0077; G12M 41/12; G06V 10/267
  See application file for complete search history.

(56) References Cited

FOREIGN PATENT DOCUMENTS

| CN | 201307108 Y | * | 9/2009 | |
|---|---|---|---|---|
| CN | 203768347 U | * | 8/2014 | |
| CN | 108303751 A | * | 7/2018 | ............. G01J 5/00 |
| CN | 110686779 A | | 1/2020 | |
| CN | 111990501 A | * | 11/2020 | |
| CN | 213067948 U | * | 4/2021 | |
| JP | 2020108731 A | * | 7/2020 | |
| JP | 2020108731 A | | 7/2020 | |

* cited by examiner

*Primary Examiner* — Gail Kaplan Verbitsky
(74) *Attorney, Agent, or Firm* — Bayramoglu Law Offices LLC

(57) ABSTRACT

A device for measuring the internal temperature of heap fermentation includes an infrared thermal imaging camera, a distance detection camera, and a controller. The infrared thermal imaging camera obtains a temperature distribution image of a surface of a fermentation heap. The distance detection camera obtains a distance between the surface of the fermentation heap and the distance detection camera. The controller matches the temperature distribution image of the surface of the fermentation heap with the distance between the surface of the fermentation heap and the distance detection camera, performs semantic segmentation on the image after matching is completed, extracts a three-dimensional (3D) contour temperature map of the surface of the fermentation heap, corrects a surface temperature of the fermentation heap, and predicts an estimated internal temperature of the fermentation heap, such that the internal temperature of the fermentation heap is effectively and accurately predicted.

8 Claims, 3 Drawing Sheets

METHOD AND DEVICE FOR MEASURING INTERNAL TEMPERATURE OF HEAP FERMENTATION BASED ON INFRARED TEMPERATURE MEASUREMENT

CROSS REFERENCE TO THE RELATED APPLICATIONS

This application is based upon and claims priority to Chinese Patent Application No. 202011450862.6, filed on Dec. 11, 2020, the entire contents of which are incorporated herein by reference.

TECHNICAL FIELD

The present invention belongs to the technical field of detection, and in particular relates to a method and device for measuring an internal temperature of heap fermentation based on infrared temperature measurement.

BACKGROUND

During production of organic substrates, temperature is an important parameter that characterizes the fermentation state of a fermentation heap, so it needs to be acquired frequently, such that the staff or automatic control equipment can control the state of heaps in time. The fermentation process of the heaps is a biological process reaction. Living microorganisms in the heaps have very strict requirements on the temperature during fermentation. Too low temperature affects the activity of the microorganisms, and too high temperature leads to the dormancy or even death of the microorganisms. Therefore, whether the temperature inside the fermentation heap can be known in real time has an important impact on the production and operation of the entire fermentation heap.

In recent years, great progress has been made in temperature detection technology around the world, especially in infrared thermal imaging temperature measurement. Due to the emergence of new materials, the miniaturization, integration and detection accuracy of a probe have been greatly improved than before. The infrared thermal imaging temperature measurement has become one of the main means of temperature measurement.

At present, in terms of temperature measurement of the fermentation heap, only an infrared thermal imager can measure the temperature without contacting the heaps. However, the infrared thermal imager can only detect the surface temperature of a measured object, there is a certain difference between the internal temperature and the surface temperature of the fermentation heap during fermentation, and the infrared thermal imager itself is affected by a measuring distance when measuring the temperature, resulting in deviation. Therefore, when the infrared thermal imager is used to detect the internal temperature of the fermentation heap, some algorithms are needed to correct its detection accuracy, and the internal temperature can be predicted by the surface temperature.

SUMMARY

In view of the shortcomings in the prior art, the present invention provides a method and device for measuring an internal temperature of heap fermentation based on infrared temperature measurement, which can effectively and accurately predict the internal temperature of a fermentation heap according to a surface temperature of the fermentation heap.

The above technical objective of the present invention is achieved by the following technical means.

A method for measuring an internal temperature of heap fermentation based on infrared temperature measurement is provided, including: matching, by a controller, a temperature distribution image of a surface of a fermentation heap with a distance between the surface of the fermentation heap and a distance detection camera, performing semantic segmentation on the image after the matching is completed, extracting a three-dimensional (3D) contour temperature map of the surface of the fermentation heap, correcting a surface temperature of the fermentation heap, and predicting an estimated internal temperature of the fermentation heap Further, distance influence correction of the surface temperature of the fermentation heap specifically includes establishing a relational model between a corrected temperature and a measured temperature and a measured distance as follows:

$$T'(T, L) = \sum_{k=0}^{b} \sigma_k u_k(T) v_k(L),$$

where $T'(T, L)$ is the corrected temperature, $T$ is the measured temperature, $L$ is the distance between the surface of the fermentation heap and the distance detection camera, $\sigma_k$ is an element of a singular matrix, $u_k(T)$ is a function of an element in a vector $u_k$ with respect to $T$, $v_k(L)$ is a function of an element in a vector $v_k$ with respect to $L$, and $b$ is an integer.

Further, predicting the estimated internal temperature of the fermentation heap is based on the following relational model:

$$T_{internal}(s) = \frac{H \sum w_{internal\ BVS}(s) - \left(m_{surface} c \sum T'(s) - H \sum w_{BVS}(s) + KA_1 \sum T'(s) - T_{enviroment}(s)\right)\right)}{m_{internal} c} - \sum T_{internal}(s-1),$$

where $H$ is biochemical reaction heat, $w_{internal\ BVS}(S)$ is a content of organic matters inside the fermentation heap, $m_{surface}$ is a total mass of the surface of the fermentation heap, $c$ is a specific heat capacity of the fermentation heap, $T'(s)$ is a surface temperature of the fermentation heap corrected at a time $s$, $w_{BVS}(s)$ is a content of the organic matters in the surface of the fermentation heap, $K$ is a thermal conductivity of air, $A_1$ is a heat transfer area, $T_{environment}(s)$ is an environment temperature at the time $s$, $m_{internal}$ is a total mass inside the fermentation heap, and $T_{internal}(s)$ is an estimated internal temperature of the fermentation heap during an s-th sampling of an infrared thermal imaging camera.

A device for measuring an internal temperature of heap fermentation includes a display screen, a control box, and a connecting groove. The display screen is arranged on a first side of the control box, the connecting groove is welded to a second side of the control box, and the control box is fixedly connected to a moving support through the connecting groove. An infrared thermal imaging camera, a distance detection camera, and a controller are arranged inside the control box, and the infrared thermal imaging camera and the distance detection camera are each connected to the controller. The controller matches a temperature distribution image obtained by the infrared thermal imaging camera with a distance obtained by the distance detection camera, extracts a 3D contour temperature map of a surface of a fermentation heap, corrects a surface temperature of the fermentation heap, and predicts an estimated internal temperature.

The moving support includes a self-propelled moving support and a suspended moving support.

The control box is fixed on a self-propelled mounting support through the connecting groove, the self-propelled mounting support is connected to the self-propelled moving support through a telescopic rod, and a roller is arranged at a bottom of the self-propelled moving support. A camera lens on the control box faces a top of a stacking-type fermentation heap.

The control box is fixed on a suspended mounting support through the connecting groove, the suspended mounting support is connected below the suspended moving support, a grooved pulley arranged on a top of the suspended moving support is matched with a suspension, a motor is further arranged on the top of the suspended moving support, and a gear on an output shaft of the motor is meshed with a gear arranged on a rotating shaft of the grooved pulley. A camera lens on the control box faces a top of a stacking-type fermentation heap.

A battery is further arranged inside the control box, the battery is connected to the controller, and the controller is further connected to a power interface.

The present invention has the following beneficial effects.

(1) In the present invention, the controller matches the temperature distribution image of the surface of the fermentation heap obtained by the infrared thermal imaging camera with the distance between the surface of the fermentation heap and the distance detection camera, performs semantic segmentation on the image after matching is completed, extracts the 3D contour temperature map of the surface of the fermentation heap, corrects the surface temperature of the fermentation heap, and predicts the estimated internal temperature of the fermentation heap by the corrected surface temperature of the fermentation heap, such that the internal temperature of the fermentation heap can be effectively and accurately predicted.

(2) In the device for measuring the internal temperature of heap fermentation according to the present invention, the control box is fixedly connected to the self-propelled or suspended moving support through the connecting groove on one side of the control box, the fermentation heaps with different fermentation modes such as stacking and trough stacking are detected, and the device convenient and flexible to use.

Figure 1:
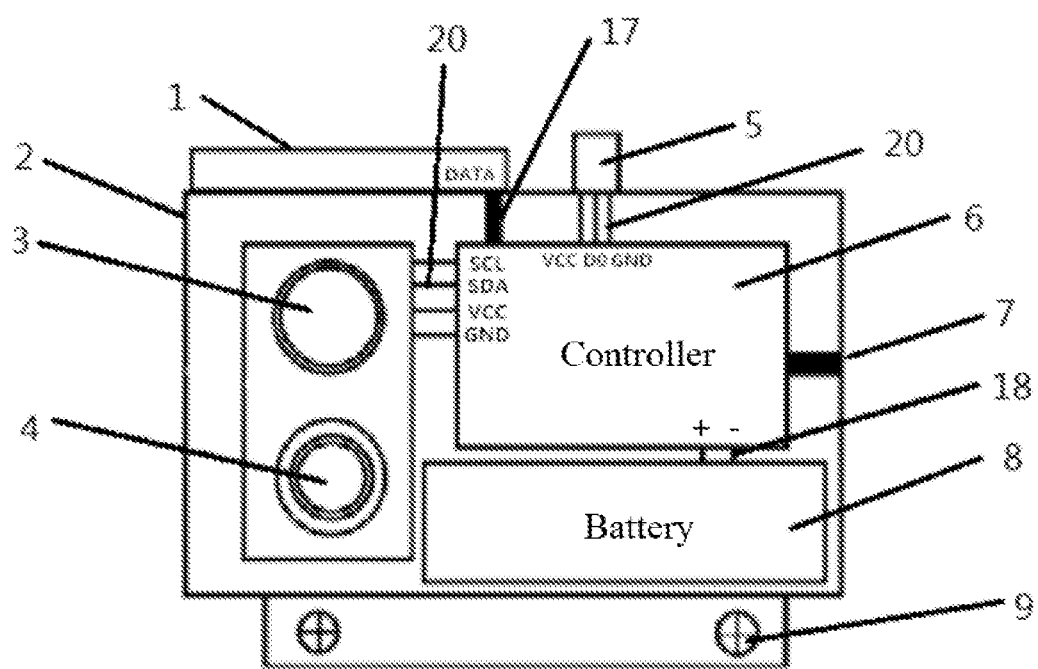
FIG. 1 is a schematic structural diagram of a device for measuring an internal temperature of heap fermentation based on infrared temperature measurement according to the present invention.
Figure 2:
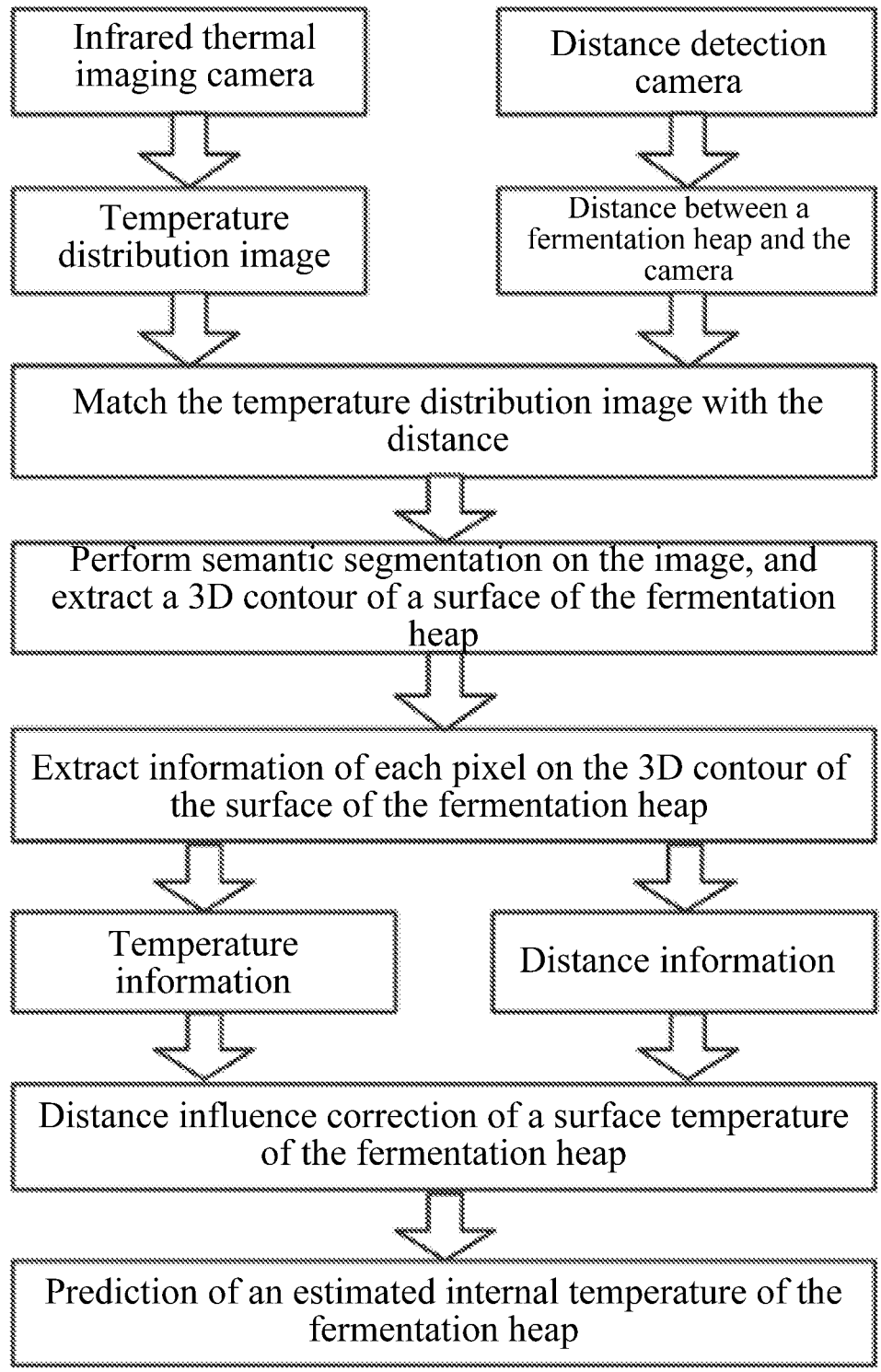
FIG. 2 is a flow chart of a method for measuring an internal temperature of heap fermentation based on infrared temperature measurement according to the present invention.

In the drawings, 1—display screen; 2—control box; 3—infrared thermal imaging camera; 4—distance detection camera; 5—thermometer; 6—controller; 7—power interface; 8—battery; 9—connecting groove; 10—self-propelled mounting support; 11—self-propelled moving support; 12—stacking-type fermentation heap; 13—suspended moving support; 14—suspension; 15—suspended mounting support; 16—trough-stacking-type fermentation heap; 17—video output line; 18—internal power supply line; 19—roller; 20—internal data line; 21—grooved pulley; 22—motor; and 23—gear.

DETAILED DESCRIPTION OF THE EMBODIMENTS

The present invention will be further described in detail below with reference to the drawings and embodiments, but the protection scope of the present invention is not limited thereto.

As shown in FIG. 1, a device for measuring an internal temperature of heap fermentation based on infrared temperature measurement according to the present invention includes a display screen 1, a control box 2, and a connecting groove 9. The display screen 1 is connected to the control box 2 through a video output line 17. The connecting groove 9 is welded to a first side of the control box 2. The control box 2 is fixedly connected to a moving support through the connecting groove 9.

A thermometer 5 and the display screen 1 are arranged on a second side of the control box 2. An infrared thermal imaging camera 3, a distance detection camera 4, a controller 6, and a battery 8 are arranged inside the control box 2. Lenses of the infrared thermal imaging camera 3 and the distance detection camera 4 extend out of the control box 2. The controller 6 is connected to the infrared thermal imaging camera 3, the distance detection camera 4, and the thermometer 5 through an internal data line 20. The battery 8 is connected to the controller 6 through an internal power supply line 18. A power interface 7 is connected to the controller 6 and charges the battery 8 through the internal power supply line 18. The controller 6 is connected to the display screen 1 through the video output line 17. The infrared thermal imaging camera 3 obtains an image characterizing temperature distribution of a surface of a fermentation heap through a temperature of each pixel in the taken image of the surface of the fermentation heap. The distance detection camera 4 obtains a distance between the surface of the fermentation heap and the distance detection camera 4 by measuring the image of the surface of the fermentation heap. The thermometer 5 is used to obtain an environment temperature around the measuring device. The controller 6 matches the temperature distribution image obtained by the infrared thermal imaging camera 3 with the distance obtained by the distance detection camera 4, extracts a 3D contour temperature map of the surface of the fermentation heap, corrects a surface temperature of the fermentation heap and predicts an estimated internal temperature based on the temperature of each pixel and the distance on the contour temperature map, and sends processed results and a composite image to the display screen 1.

A working principle of the device for measuring the internal temperature of heap fermentation based on infrared temperature measurement is: the infrared thermal imaging camera 3 uploads the obtained temperature distribution image of the surface of the fermentation heap to the controller 6, and the controller 6 matches the temperature distribution image with the distance uploaded by the distance detection camera 4, performs semantic segmentation on the image after matching is completed, extracts a 3D contour of the surface of the fermentation heap containing pixel information, temperature information, and distance information, then performs distance influence correction on the extracted 3D contour temperature, and predicts the estimated internal temperature of the fermentation heap according to the principle of heat balance in combination with the environment temperature after correction is completed.

The correction of the surface temperature of the fermentation heap and the prediction of the estimated internal temperature of the fermentation heap are specifically as follows.

Step (1), distance influence of the surface temperature of the fermentation heap is corrected.

The infrared thermal imaging camera 3 measures m groups of temperature T. The distance detection camera 4 measures n groups of distance L. The high-precision thermometer measures a true temperature T' of the surface of m×n group of fermentation heaps. The temperature, distance, and true temperature are combined into a set $\{T_i, L_j, T'_{ij}\}$ (i=0, ..., m, j=0, ..., n) to construct a matrix A of m rows and n columns with T' as an element, and singular decomposition is performed:

$$A = UIV^T \Rightarrow A(v_1, \ldots, v_n) = (u_1, \ldots, u_m) \text{diag}[\sigma_1, \ldots, \sigma_b, 0, \ldots 0] \quad (1)$$

U and V are both orthogonal matrices, and I is a singular matrix. The first b items in U and V form an m-dimensional vector $u_k = ((u_k)_1, \ldots, (u_k)_i)$ and an n-dimensional vector $v_k = ((v_k)_1, \ldots, (v_k)_j)$, k=0, ..., b (b is an integer). Coordinates $(T_i, (u_k)_i)$ and $(L_j, (v_k)_j)$ are set up, functions $u_k(T)$ and $v_k(L)$ are constructed by interpolating the above coordinates, and the formula (1) is further transformed as follows:

$$A = \sum_{k=0}^{b} \sigma_k u_k v_k^T. \quad (2)$$

$\sigma_k$ is an element of the singular matrix I. Elements in the matrix A are expressed separately, which is:

$$T'_{ij} = \sum_{k=0}^{b} \sigma_k (u_k)_i (v_k)_j. \quad (3)$$

Then the functions $u_k(T)$ and $v_k(L)$ are substituted into the formula (3) to obtain:

$$T'(T, L) = \sum_{k=0}^{b} \sigma_k u_k(T) v_k(L). \quad (4)$$

At this time, T'(T, L) is a corrected temperature.

Step (2), heat transferred from the inside of heaps to the surface of the heaps is calculated.

A heat balance formula for the surface of the fermentation heap is:

$$Q_{total\ of\ the\ surface} = Q_{reaction\ heat} + Q_{transfer} - Q_{loss} \quad (5), \text{and}$$

$$Q_{transfer} = Q_{total\ of\ the\ surface} - Q_{reaction\ heat} + Q_{loss} \quad (6).$$

$Q_{total}$ of the surface is heat of the surface part of the fermentation heap, $Q_{reaction\ heat}$ is heat generated by the fermentation heap itself, $Q_{transfer}$ is the heat transferred from the inside of the fermentation heap to the surface, and $Q_{loss}$ is heat lost by heat exchange between the surface of the fermentation heap and air. The heat expression of each link is:

$$Q_{total\ of\ the\ surface} = m_{surface} c \int T(t) dt$$

$$m_{surface} = \rho V_{surface}$$

$$V_{surface} = DW H_{surface} \quad (7).$$

$m_{surface}$ is a total mass of the surface of the fermentation heap, c is a specific heat capacity of the fermentation heap, T'(t) is a surface temperature of the fermentation heap corrected at a time t, t is the time, $\rho$ is a density of the heaps of the fermentation heap, $V_{surface}$ is a total volume of the surface part of the fermentation heap, D is a length of a fermentation heap tank, W is a width of the fermentation heap tank, and $H_{surface}$ is a thickness of the surface part of the fermentation heap.

According to a biodegradation kinetic equation, the heat generated by the fermentation heap itself may be expressed as:

$$Q_{reaction\ heat} = H \int w_{BVS}(t) dt \quad (8).$$

$w_{BVS}(t)$ is a content of organic matters in the surface of the fermentation heap, H is biochemical reaction heat, and the content of the organic matters in the surface of the fermentation heap decreases with the fermentation process, and may be expressed by a logistic equation as:

$$w_{BVS}(t) = w_{end} + \frac{w_0 - w_{end}}{1 + \exp\left[\frac{(t - k_0)}{k_1}\right]}. \quad (9)$$

$w_{end}$ is a content of the organic matters in the surface part after fermentation, $w_0$ is a content of the organic matters in the surface before fermentation, and $k_0$ and $k_1$ are fixed parameters, and are obtained by substituting the remaining parameters ($w_{BVS}(t)$, $w_{end}$, $w_0$, and t) into the formula (9).

According to a heat transfer equation, the lost heat may be expressed as:

$$Q_{loss} = K A_1 \int (T'(t) - T_{environment}(t)) dt \quad (10).$$

K is a thermal conductivity of air, $A_1$ is a heat transfer area, $T_{environment}(t)$ is an environment temperature at the time t.

According to the formulas (6) to (10), the heat $Q_{transfer}$ transferred from the inside of heaps to the surface of the heaps can be calculated.

Step (3), an internal temperature of the heaps is estimated.

An internal heat balance formula of the fermentation heap is:

$$Q_{total\ of\ the\ inside} = Q_{internal\ reaction\ heat} - Q_{transfer} \quad (11).$$

$Q_{total\ of\ the\ inside}$ is total heat inside the fermentation heap, and $Q_{internal\ reaction\ heat}$ is heat generated by the inside of the fermentation heap itself.

The total heat inside the fermentation heap may be expressed as:

$$Q_{total\ of\ the\ inside} = m_{internal} c \int T_{internal}(t) dt$$

$$m_{internal} = \rho V_{internal}$$

$$V_{internal} = DWH_{internal} \quad (12).$$

$m_{internal}$ is a total mass inside the fermentation heap, $T_{internal}(t)$ is an internal temperature of the fermentation heap at the time t, $V_{internal}$ is a total volume inside the fermentation heap, and $H_{internal}$ is a thickness inside the fermentation heap.

The heat generated by the inside of the fermentation heap itself may be expressed as:

$$Q_{internal\ reaction\ heat} = H \int w_{internal\ BVS}(t) dt, \text{ and} \quad (13)$$

$$w_{internal\ BVS}(t) = w_{internal\ end} + \frac{w_{internal\ 0} - w_{internal\ end}}{1 + \exp\left[\frac{(t-k_2)}{k_3}\right]}. \quad (14)$$

$w_{internal\ BVS}(t)$ is a content of the organic matters inside the fermentation heap, $w_{internal\ end}$ is a content of the organic matters inside the fermentation heap after fermentation, $w_{internal\ 0}$ is a content of the organic matters inside the fermentation heap before fermentation, and $k_2$ and $k_3$ are fixed parameters, and are obtained by substituting the remaining parameters ($w_{internal\ end}$, $w_{internal\ 0}$, $w_{internal\ BVS}(t)$, and t) into the formula (14).

The formula (6) is substituted into the formula (11) to obtain:

$$Q_{total\ of\ the\ inside} = Q_{internal\ reaction\ heat} - (Q_{total\ of\ the\ surface} - Q_{reaction\ heat} + Q_{loss}) \quad (15).$$

The heat expression of each link is substituted into the formula (14) to obtain:

$$m_{internal} c \int T_{internal}(t) dt = H \int w_{internal\ BVS}(t) dt - (m_{surface} c \int T_{surface}(t) dt - H \int w_{BVS}(t) dt + KA_1 \int (T_{surface}(t) - T_{environment}(t)) dt) \quad (16).$$

The formula (16) is discretized to obtain:

$$m_{internal} c \Sigma T_{internal}(s) = H \Sigma_{internal\ BVS}(s) - (m_{surface} c \Sigma T(s) - H \Sigma w_{BVS}(s) + KA_1 \Sigma (T(s) - T_{environment}(s))) \quad (17).$$

The formula (17) is deformed to obtain:

$$T_{internal}(s) = \frac{H \sum w_{internal\ BVS}(s) - \left(m_{surface} c \sum T'(s) - H \sum w_{BVS}(s) + KA_1 \sum T'(s) - T_{enviroment}(s)\right)}{m_{internal} c} - \sum T_{internal}(s-1). \quad (18)$$

s is an integer from 0 to infinity, and $T_{internal}(s)$ is an estimated internal temperature of the fermentation heap during an s-th sampling of the infrared thermal imaging camera 3.

Embodiment 1

Figure 3:
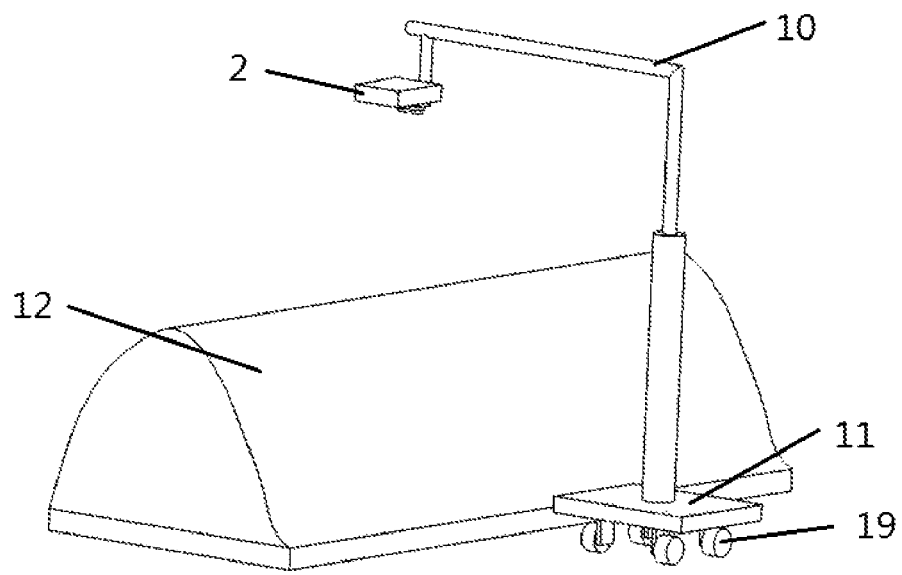
FIG. 3 is a schematic diagram of self-propelled detection of the device for measuring the internal temperature of heap fermentation based on infrared temperature measurement according to the present invention.

The present embodiment is a self-propelled detection method for a stacking-type fermentation heap 12 of a device for measuring an internal temperature of heap fermentation based on infrared temperature measurement according to the present invention. As shown in FIG. 3, the overall structure of the device for measuring the internal temperature of heap fermentation includes a control box 2, a self-propelled mounting support 10, a self-propelled moving support 11, and a roller 19. The control box 2 is installed as follows: a camera lens faces the surface of the stacking-type fermentation heap 12, the control box 2 is connected and fixed to the self-propelled mounting support 10, the self-propelled mounting support 10 is connected to the self-propelled moving support 11 through a telescopic rod that can be adjusted up and down, and the movable roller 19 is arranged at the bottom of the self-propelled moving support 11. A working mode of the device is: the roller 19 drives the device to move linearly along the side of the stacking-type fermentation heap 12, a camera lens on the control box 2 always faces a top of the stacking-type fermentation heap 12, and the control box 2 continuously obtains a surface distribution image of the stacking-type fermentation heap 12 and a distance between the fermentation heap and a distance detection camera 4 while following the movement of the self-propelled moving support 11, and estimates the internal temperature of the fermentation heap.

Embodiment 2

Figure 4:
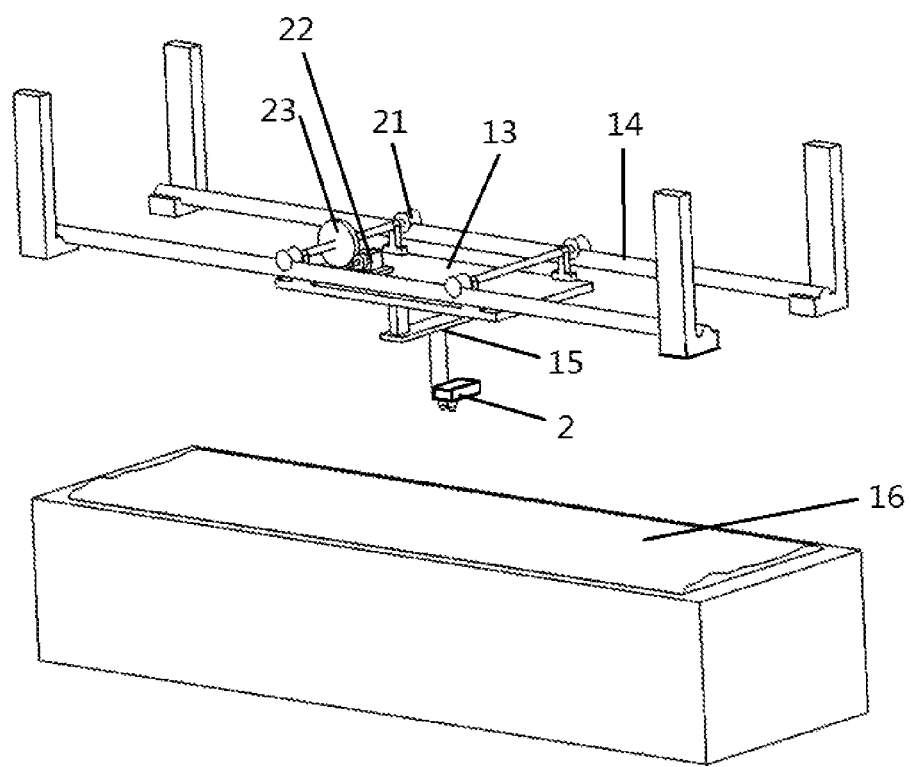
FIG. 4 is a schematic diagram of suspended detection of the device for measuring the internal temperature of heap fermentation based on infrared temperature measurement according to the present invention.

The present embodiment is a suspended detection method for a trough-stacking-type fermentation heap 16 of a device for measuring an internal temperature of heap fermentation based on infrared temperature measurement according to the present invention. As shown in FIG. 4, the overall structure of the device for measuring the internal temperature of heap fermentation includes a control box 2, a suspended mounting support 15, a suspended moving support 13, and a suspension 14. The control box 2 is installed as follows: a camera lens faces the trough-stacking-type fermentation heap 16, the control box 2 is connected and fixed to the suspended mounting support 15, the suspended mounting support 15 is connected below the suspended moving support 13, a grooved pulley 21 is arranged on a top of the suspended moving support 13, the grooved pulley 21 is movable on the suspension 14, a motor 22 is arranged on the top of the suspended moving support 13, a gear 23 is arranged on a rotating shaft of the grooved pulley 21, and a gear on an output shaft of the motor 22 is meshed with the gear 23. A working mode of the device is: the motor 22 drives the grooved pulley 21 through the gear 23, such that the grooved pulley 21 moves linearly along the suspension 14, a camera lens on the control box 2 always faces a top of a trough of the trough-stacking-type fermentation heap 16, and the control box 2 continuously obtains a surface distribution image of the trough-stacking-type fermentation heap 16 and a distance between the fermentation heap and a distance detection camera 4 while following the movement of the suspended mounting support 15, and estimates the internal temperature of the fermentation heap.

The above embodiments are preferred implementations of the present invention, but the present invention is not limited to the above implementations. Any obvious improvement, substitution or modification made by those skilled in the art without departing from the essence of the present invention should fall within the protection scope of the present invention.

What is claimed is:

1. A method for measuring an internal temperature of heap fermentation based on infrared temperature measurement, comprising:
matching, by a controller, a temperature distribution image of a surface of a fermentation heap with a distance between the surface of the fermentation heap and a distance detection camera;
performing semantic segmentation on the temperature distribution image after the matching is completed;
extracting a three-dimensional (3D) contour temperature map of the surface of the fermentation heap;
correcting a surface temperature of the fermentation heap; and
predicting an estimated internal temperature of the fermentation heap;
wherein, the step of predicting the estimated internal temperature of the fermentation heap is based on the following relational model:

$$T_{internal}(s) = \frac{H\sum w_{internal\ BVS}(s) - \left(m_{surface}c\sum T'(s) - H\sum w_{BVS}(s) + KA_1 \sum T'(s) - T_{enviroment}(s)\right)}{m_{internal}c} - \sum T_{internal}(s-1),$$

wherein H is biochemical reaction heat, $w_{internal\ BVS}(S)$ is a content of organic matters inside the fermentation heap, $m_{surface}$ is a total mass of the surface of the fermentation heap, c is a specific heat capacity of the fermentation heap, T'(s) is a surface temperature of the fermentation heap corrected at a time s, $w_{BVS}(S)$ is a content of the organic matters in the surface of the fermentation heap, K is a thermal conductivity of air, $A_1$ is a heat transfer area, $T_{environment}(s)$ is an environment temperature at the time s, $m_{internal}$ is a total mass inside the fermentation heap, and $T_{internal}(s)$ is an estimated internal temperature of the fermentation heap during an s-th sampling of an infrared thermal imaging camera.

2. The method for measuring the internal temperature of the heap fermentation according to claim 1, wherein
distance influence correction of the surface temperature of the fermentation heap specifically comprises: establishing a relational model between a corrected temperature and a measured temperature and a measured distance as follows:

$$T'(T, L) = \sum_{k=0}^{b} \sigma_k u_k(T) v_k(L),$$

wherein T'(T, L) is the corrected temperature, T is the measured temperature, L is the distance between the surface of the fermentation heap and the distance detection camera, $\sigma_k$ is an element of a singular matrix, $u_k(T)$ is a function of an element in a vector $u_k$ with respect to T, $v_k(L)$ is a function of an element in a vector $v_k$ with respect to L, and b is an integer.

3. A measuring device for the method for measuring the internal temperature of the heap fermentation according to claim 1, comprising a display screen, a control box, and a connecting groove, wherein
the display screen is arranged on a first side of the control box, the connecting groove is welded to a second side of the control box, and the control box is fixedly connected to a moving support through the connecting groove;
the infrared thermal imaging camera, the distance detection camera, and the controller are arranged inside the control box, and the infrared thermal imaging camera and the distance detection camera are connected to the controller; and
the controller matches the temperature distribution image obtained by the infrared thermal imaging camera with the distance obtained by the distance detection camera, extracts the 3D contour temperature map of the surface of the fermentation heap, corrects the surface temperature of the fermentation heap, and predicts the estimated internal temperature.

4. The measuring device according to claim 3, wherein the moving support comprises a self-propelled moving support and a suspended moving support.

5. The measuring device according to claim 4, wherein the control box is fixed on a self-propelled mounting support through the connecting groove, the self-propelled mounting support is connected to the self-propelled moving support through a telescopic rod, and a roller is arranged at a bottom of the self-propelled moving support; and a camera lens on the control box faces a top of a stacking-type fermentation heap.

6. The measuring device according to claim 4, wherein the control box is fixed on a suspended mounting support through the connecting groove, the suspended mounting support is connected below the suspended moving support, a grooved pulley arranged on a top of the suspended moving support is matched with a suspension, a motor is further arranged on the top of the suspended moving support, and a gear on an output shaft of the motor is meshed with a gear arranged on a rotating shaft of the grooved pulley; and a camera lens on the control box faces a top of a stacking-type fermentation heap.

7. The measuring device according to claim 3, wherein a battery is further arranged inside the control box, the battery is connected to the controller, and the controller is further connected to a power interface.

8. The measuring device according to claim 3, wherein distance influence correction of the surface temperature of the fermentation heap specifically comprises: establishing a relational model between a corrected temperature and a measured temperature and a measured distance as follows:

$$T'(T, L) = \sum_{k=0}^{b} \sigma_k u_k(T) v_k(L),$$

wherein T'(T, L) is the corrected temperature, T is the measured temperature, L is the distance between the surface of the fermentation heap and the distance detection camera, $\sigma_k$ is an element of a singular matrix, $u_k(T)$ is a function of an element in a vector $u_k$ with respect to T, $v_k(L)$ is a function of an element in a vector $v_k$ with respect to L, and b is an integer.

* * * * *